United States Patent [19]
Dobrescu et al.

[11] 4,136,181
[45] Jan. 23, 1979

[54] VACCINES AGAINST OEDEMA DISEASE OF PIGLETS

[75] Inventors: Lucia Dobrescu, Brussels; Constant Huygelen, Huldenberg; Frans Van Wijnendaele, Ottenburg, all of Belgium

[73] Assignee: Recherche et Industrie, Therapeutiques, RIT, Belgium

[21] Appl. No.: 865,451

[22] Filed: Dec. 29, 1977

Related U.S. Application Data

[63] Continuation-in-part of Ser. No. 715,746, Aug. 18, 1976, abandoned.

[51] Int. Cl.² .................... A61K 39/00; A61K 39/02
[52] U.S. Cl. ...................................................... 424/92
[58] Field of Search ........................................ 424/92

[56] References Cited
U.S. PATENT DOCUMENTS

| | | | |
|---|---|---|---|
| 2,125,533 | 8/1938 | Winegarden et al. | 424/92 |
| 3,208,909 | 9/1965 | Puziss et al. | 424/92 |
| 3,983,229 | 9/1976 | Relyveld | 424/92 |
| 4,002,736 | 1/1977 | Pankratz | 424/92 |
| 4,053,584 | 10/1977 | Dobrescu et al. | 424/92 |

OTHER PUBLICATIONS

Kamzolkina, C.A., 76 #70857c (1972) of ZH. Mikrobiol. Epidemiol, Immunobiol. (1971) 48 (11):49-54.
Kamzolkina, C.A. 74 #109847k (1971) of Byull. Eksp. Biol. Med. (1971) 71 (2):70-73.
Schimmelpfennig, C.A. 77 #1549n (1972) of Zentralbl. Veterinairmed. Reihob. (1971) 18(8):622-633.
Sourek et al., C.A. 78 #94032x (1973) of Ann. Microbiol (Paris) (1973) 124A(1):45;14 60.
Digeon et al., C.A. 81 #167720u (1974) of Ann. Immunol. (Paris) (1974):125C(4):611-623.

*Primary Examiner*—Shep K. Rose
*Attorney, Agent, or Firm*—Janice E. Williams; William H. Edgerton; Alan D. Lourie

[57] ABSTRACT

Vaccines against oedema disease of piglets comprising an effective amount of *E. coli* neurotoxin isolated from a culture of an *E. coli* serotype which is capable of causing piglet oedema disease and adsorbed on an adjuvant. The vaccines are administered by intramuscular or subcutaneous route.

5 Claims, No Drawings

VACCINES AGAINST OEDEMA DISEASE OF PIGLETS

This application is a continuation-in-part of our co-pending application Ser. No. 715,746 filed Aug. 18, 1976, now abandoned.

The present invention relates to vaccines against oedema disease of piglets.

Oedema disease of piglets also known "bowel oedema" or "enterotoxemia" is an acute disease, the clinical symptoms of which are ataxia, convulsions, partial or complete paralysis, anatomopathological features being oedema of various organs, principally the stomach wall, the mesentery of the spiral colon and the brain.

Various theories have been put forward regarding the aetiology of the disease. Piglet oedema disease is now known to be caused by a specific toxin-named neurotoxin-elaborated by pathogenic strains of Escherichia coli.

In Res. Vet. sci. 1 : 17-27, 1960 W. J. Sojka describes the most common *E. coli* serotypes isolated in piglet oedema disease cases and in Zbl. Vet. Med. (B) 18 : 622-33, 1971 H. Schimmelpfennig indicates that the neurotoxin is produced by the predominant *E. coli* serotypes isolated from oedema disease in piglets, i.e. the 0138, 0139 and 0141 serotypes.

Several authors have suggested that neurotoxin could be the lipoproteinic fraction of the whole *E. coli* endotoxin complex (Van Haeringen H. Thesis : *E. coli* infecties bij biggen, frequentie en pathogeniteit van verschillende typen, Utrecht 1974; Schimmelpfennig H. : Untersuchungen zur aetiologie des Odemkrankheit des Schweines. Verlag Paul Parey, Berlin und Hamburg 1970; Mesrobeanu L. & al. : Ann. N.Y. Acad. Sci. 133 (2) : 685-99, 1966) but the attempts to separate the neurotoxin from the endotoxin complex were unsuccessful (Schimmelpfennig H., Zbl. Vet. Med. loc. cit.).

Active immunization against piglet oedema disease has been attempted with various *E. coli* preparations consisting of either whole *E. coli* organisms or lysates thereof (W. J. Sojka, "*E. coli* in domestic animals and poultry" edited by the Commonwealth Agricultural Bureau, 1965, p. 124; E. Kauker, Deuts. Tieraerzt. Wochensch. 78 : 182-84, 1971 and K. Lutter, Monatsh. Veterinaermed. 29 : 694-99, 1974) but these preparations either fail to protect the piglets or only induce a serotype specific immunity corresponding to the *E. coli* serotype used in the preparation.

Using either the gel filtration technique on crosslinked-dextran (Sepharose-6B ®) or the chromatography technique on aluminium hydroxide-cellulose we have isolated the *E. coli* neurotoxin responsible for piglet oedema disease.

Moreover, we have surprisingly found that, when isolating the *E. coli* neurotoxin in purified form (i.e. substantially free from endotoxin) from a culture of an *E. coli* serotype which is capable of causing oedema disease of piglet—e.g. the 0138, 0139 or 0141 serotype—and administering the isolated neurotoxin with an adjuvant by subcutaneous or intramuscular route to piglets, the animals are effectively protected against oedema disease.

In Ann. Biol. Inst. Pasteur 124 A : 45-60, 1973, J. Sourek et al. described a method for isolating toxins from *Shigella dysenteriae* (Shiga) by gel filtration on crosslinked-dextran (Sepharose ®-4B) followed by ion-exchange chromatography (on DEAE-cellulose). By this method, Sourek et al. isolated in a purified form the Shiga endotoxin and a toxin which, owing to its neurotoxicity (limb paralysis) on mice was already known as 'Shiga neurotoxin' and, in Ann. Immunol. Inst. Pasteur 125 C : 611-23, 1974, M. Digeon et al. described the immunization of rabbits, guinea pigs and horses with preparations of these 'Shiga endotoxin' and 'Shiga neurotoxin' against the same toxins, respectively.

In J. of Inf. Dis. 131 S : 33-39, 1975 G. T. Keusch and M. Jacewicz pointed out that the use of a clinically relevant animal model, the rabbit ileal loop, for the study of bacterial enterotoxins had resulted in the discovery of a protein enterotoxin produced by *Shigella dysenteriae* (Shiga) and indicated that what had been referred to in the literature as Shiga neurotoxin was the same partially purified mixture of proteins as the Shiga product that had been called enterotoxin. Consequently, it is likely that Shiga neurotoxin originally would have been named Shiga enterotoxin, had the ileal loop assay been available at that time.

In Zbl. Vet. Med. (loc. cit.) H. Schimmelpfennig indicated that antiserum prepared from a crude *E. coli* neurotoxin preparation protects mice against mortality resulting from inoculation of the same crude. Nevertheless, since said crude product causes mortality without any other symptom in the control animals, it may not be deduced that the cause of mortality was neurotoxin but rather that the cause of mortality was residual endotoxin in the crude product. In other words, the reference does not suggest anything regarding an eventual immunogenic effect of the *E. coli* neurotoxin.

Since there is no systematic relationship between toxicity and immunogenicity (for instance, as indicated by H. W. Smith and C. L. Gyles in J. Med. Microbiol. 3 : 387-401, 1969, the *E. coli* ST enterotoxin is toxic but not immunogenic) it was even not obvious that pure *E. coli* neurotoxin was immunogenic.

An essential feature of the present invention thus resides in the isolation of *E. coli* neurotoxin in purified form and its use as a vaccine for protecting piglets against oedema disease.

As a matter of fact, contrary to the previously known *E. coli* neurotoxin preparations, the *E. coli* neurotoxin of the invention is substantially free from the endotoxin contaminant which is known to be a non negligible cause of severe anaphylactic shocks (as indicated for instance by B. J. Shreeve and J. R. Thomlinson, J. Med. Microbiol. 4 : 307-318, 1970).

The *E. coli* neurotoxin of the invention is a product showing an average molecular weight of 100.000 when determined by gel chromatography on Sepharose-6B (Sepharose is a trademark of Pharmacia Fine Chemicals AB, Uppsala, Sweden) and obtainable from the supernatant of disrupted cells of a culture of an *E. coli* serotype capable of causing oedema disease of piglets—examples of which are *E. coli* 0138, 0139 and 0141 serotypes—the process comprising precipitating thereof crude neurotoxin by ammonium sulfate, dialysing it in cellophane bags against running water, sterilizing the solution, dissolving the crude extract in aqueous buffer (e.g. 0.2 M tris-(hydroxymethyl)-amino methane/hydrochloric acid (Tris-HCl) buffer at pH 8 supplemented with 0.15 M sodium chloride) and sodium dodecyl sulfate (SDS) 1%, applying the solution onto a chromatography column containing a crosslinked dextran gel (e.g. Sepharose ® 6B, a product of Pharmacia Fine Chemicals AB, Uppsala, Sweden), performing the elution with Tris-NaCl and concentrating by ultrafiltration—more particularly on Diaflo ® membrane (a product of Amicon) — the fraction showing an average molecular weight of 100,000.

For preparing a vaccine according to the invention, the pH of the concentrated solution is adjusted to 6.3 (± 0.1) e.g. with normal hydrochloric acid and the solution is absorbed up to saturation and preferably at the saturation on an adjuvant product or composition selected from the group consisting of aluminium hydroxide and aluminium phosphate, more particularly on Alhydrogel (an aluminium hydroxide gel manufactured and sold by Superfos Export Co., Copenhagen, Denmark).

The neurotoxin/adjuvant ratio is preferably calculated for maximum adsorption of the neurotoxin on the adjuvant (see Symp. Series Immunobiol. Standard 6 : 173-180, 1967).

For instance, to one volume of concentrated neurotoxin solution containing 4 mg of protein per milliliter, there is added 0.4 volume of a 2% aqueous solution of Alhydrogel and the adsorption of the neurotoxin on Alhydrogel is controlled by precipitation test with trichloroacetic acid. Alternatively, adsorption on an aluminium hydroxide adjuvant (e.g. chromatography on aluminium hydroxide-powdered cellulose mixture) can also be used instead of gel filtration on Sepharose 4-B for separating $E.$ $coli$ endotoxin from $E.$ $coli$ neurotoxin.

The vaccines of the invention thus comprise an effective amount of $E.$ $coli$ neurotoxin isolated from a culture of an $E.$ $coli$ serogroup which is capable of causing piglet oedema disease—for instance the 0138, 0139 and 0141 serogroup—more particularly the 0139 serogroup as the $E.$ $coli$ strain ATCC 31165- adsorbed on an effective amount of an adjuvant product or composition selected from the group consisting of aluminium hydroxide and aluminium phosphate—more particularly an aluminium hydroxide gel, such as Alhydrogel—the effective amount of $E.$ $coli$ neurotoxin being at least 80 mg calculated on the basis of its protein contents.

According to the invention, the vaccine containing an effective amount of $E.$ $coli$ neurotoxin as hereinabove described is administered to piglets by intramuscular or subcutaneous route. An $E.$ $coli$ strain suitable as starting material for performing the present invention has been deposited at the American Type Culture Collection where it received accession number ATCC 31165.

The following examples illustrate the invention; they should not be construed as limiting its scope.

EXAMPLE 1

Preparation of Crude Neurotoxin (a) Seed Preparation $E.$ $coli$ strain ATCC 31165 is rehydrated with sterile saline and incubated for 18 hours at 37° C. in Petri dishes containing each 20 ml of TRYPTOSE-AGAR solid medium prepared by mixing 26 g of TRYPTOSE broth, 30 g of AGAR Difco (TRYPTOSE broth and AGAR Difco are products manufactured and sold by Difco Labs) and water up to one liter, the mixture being heated for 45 minutes at 115° C.

A liquid culture medium (named PP$_3$) is then prepared as follows : Proteose peptone No. 3 (a product manufactured and sold by Difco Labs) 30 g, yeast extract (4 g) and dextrose (5 g) are dissolved in one liter of water at 60° C. After cooling, NaCl (5 g) NaHPO$_4$ (5.05 g) and KH$_2$PO$_4$ (1.2 g) are added thereto. The medium, the pH of which is 6.9–7.0 is filtered on Seitz EKS filter and distributed into 100 ml culture flasks.

These culture flasks are inoculated with the colonies obtained on Petri dishes, using one colony per 20 ml of PP$_3$ liquid medium and incubated for six hours at 37° C. with shaking on rocking shelves (22 to 24 rockings per minute).

(b) $E.$ $coli$ Production

Six milliliter aliquots of the $E.$ $coli$ containing culture medium (i.e. about $6.10^9$ bacteria) are inoculated into production flasks containing 300 ml of PP$_3$ liquid medium and the cultures are incubated for one day with shaking on rocking shelfs (22 to 24 rockings per minute).

The harvests of five production flasks (one series) are pooled and each series of harvests is centrifuged for two hours at 2,000 g, the sediment is resuspended in 150 ml. of distilled water.

The cell suspension is sonicated for 30 minutes in a Branson Europa sonicator model J 22 (Branson Europa N.V., Soest, The Netherlands), the medium being kept in a melting ice bath.

After disruption of the cells, the suspension is centrifuged for two hours at 2,000 g at 5° C. in order to eliminate the cell debris. The supernatant is passed through a 0.45 micron Millipore sterilizing filter (Millipore is a trademark of Millipore Corporation) to yield 100 ml of filtrate.

Ammonium sulfate previously sterilized by ethylene oxide is added to the filtrate up to reaching 50% saturation (380 g of ammonium sulfate per liter of filtrate) and the mixture is allowed to stand for three hours at room temperature. The obtained precipitate is centrifuged for two hours at 2,000 g at the temperature of 5° C.

The sediment is poured into a Cellophane ® cellulose acetate dialysis bag with a porosity corresponding to a molecular weight of $1-1.5 \times 10^3$ and dialyzed against running water until the concentration in ammonium sulfate is lowered to between 0.1 and 0.01% (w/v), the ammonium sulfate contents being tested with Nessler's reagent.

The neurotoxin preparation is sterilized by passage through a 0.45 micron Millipore sterilizing filter (Millipore is a trademark of Millipore Corporation) and freeze-dried.

Neurotoxin Purification

A column (2,5 × 100 cm) is packed with Sepharose ® 6-B (a product from Pharmacia Fine Chemicals AB, Uppsala, Sweden) suspended in Tris-HCl buffer (0.2 M, pH 8.0) supplemented with 0.15 M NaCl. After equilibration at 4° C., 170 mg of crude neurotoxin preparation dissolved in 5 ml Tris-NaCl buffer supplemented with 2.5 ml SDS 1% is applied to the column. The column is eluted with Tris-NaCl buffer at a velocity of 5–10 ml/hour. In the elution profile two main peaks appear, the one eluted with a volume corresponding to a molecular weight (MW) of $10^6-4.10^6$, the other one with a volume corresponding to a MW of about 100,000, both calculated by the elution volume technique.

The product with a MW of about 100,000—identified as neurotoxin by his in vivo effects—is concentrated on Diaflo ®UM 20E membrane filters (a product sold by Amicon B.V., Oosterhout, N-B., Holland).

The pH of the concentrated preparation is adjusted to 3 with normal hydrochloric acid and 0.4 volume of a 2% aqueous solution of Alhydrogel is added to one volume (4 mg of protein/ml) of neurotoxin preparation, the adsorption of the neurotoxin on the Alhydrogel being controlled by precipitation test with trichloroacetic acid. The sediment is isolated, dried and distributed into vials containing dosage units or multiples thereof.

For vaccinal use, the sediment is rehydrated with a mixture of equal volumes of Sorensen buffer ($Na_2HPO_4M/10$ : 22%, $KH_2PO_4M/10$ : 78%) pH 6.3 and normal saline.

EXAMPLE 2

In order to determine whether the neurotoxin of example 1 was free of enterotoxin, a comparative study of the biological activities of said neurotoxin and of LT enterotoxin obtained from *E. coli* strain ATCC 21972 was performed with different doses of each toxin in different assay systems specific for each toxin. The employed assay systems were the Y1 adrenal cells culture system and the rabbit loop test on the one side and paralysis in mice on the other side for the *E. coli* LT enterotoxin and the *E. coli* neurotoxin respectively.

The results are summarized in the following Table I wherein the dose variation demonstrate that the neurotoxin of example 1 is free of enterotoxin.

TABLE I

| Toxin origin | Dose of toxin (mg) | Y1 cell line (typical morphological changes) | rabbit loop IR >0.2* | mice (paralysis) |
|---|---|---|---|---|
| ATCC 21972 | 0.001 to 0.02 | + | NT | NT |
| ATCC 21972 | 1 | NT | + | NT |
| ATCC 21972 | 10 | | + | |
| ATCC 21972 | 1.5 | NT | NT | − |
| ATCC 21972 | 0.7 | | | − |
| ATCC 31165 | 0.02 | − | NT | NT |
| ATCC 31165 | 1 | | − | |
| ATCC 31165 | 10 | NT | | NT |
| ATCC 31165 | | | − | |
| ATCC 31165 | 1.5 | | | + |
| ATCC 31165 | 0.7 | NT | NT | + |

*IR means intensity of reaction (expressed in ml of fluid per cm of intestine).

EXAMPLE 3

Piglets (5 weeks old) were inoculated by subcutaneous route with 80 mg (calculated in protein content) of the Alhydrogel adjuvanted neurotoxin obtained according to the process of example 1.

A dose of 20 mg of non adjuvanted neurotoxin was injected intravenously one month later.

One week after the booster inoculation, the vaccinated piglets and the control ones were challenged intravenously with 1.5 mg/kg of neurotoxin.

The results are summarized in the following Table II.

TABLE II

| | Piglets | Results of the challenge | | | | |
|---|---|---|---|---|---|---|
| | | Mortality without previous symptoms | Eyelid oedema | Ataxia | Convulsions | Paralysis |
| Vaccinated | 1 | − | − | − | − | − |
| | 2 | − | − | − | − | − |
| | 3 | − | − | − | − | − |
| | 4 | − | − | − | − | − |
| | 5 | − | − | − | − | − |
| | 6 | − | − | − | − | − |
| Control | 7 | + | | | | |
| | 8 | − | + | + | + | + |
| | 9 | − | + | + | + | + |
| | 10 | − | + | + | + | + |
| | 11 | − | + | + | + | + |
| | 12 | − | − | − | − | − |
| | 13 | − | + | + | + | + |
| | 14 | − | + | + | + | + |

As shown in Table II, none of the vaccinated piglets presents symptoms of the oedema disease while 6 out of 8 control animals presented symptoms of the disease and one was found dead.

EXAMPLE 4

Piglets (5 weeks old) were inoculated as in example 3 but with an intravenous booster of 10.8 mg instead of 20 mg.

Two weeks after the booster injection, the vaccinated piglets and the control ones were challenged as in example 3.

The results are summarized in the following Table III.

TABLE III

| | Piglets | Results of the challenge | | | | |
|---|---|---|---|---|---|---|
| | | Mortality without previous symptoms | Eyelid oedema | Ataxia | Convulsions | Paralysis |
| Vaccinated | 15 | − | − | − | − | − |
| | 16 | − | − | − | − | − |
| | 17 | − | − | − | − | − |
| | 18 | − | − | + | + | − |
| | 19 | − | − | + | + | − |
| | 20 | − | − | − | − | − |

None of the vaccinated piglets presents symptoms of the disease while, of the control animals 2 out 3 showed symptoms.

EXAMPLE 5

Piglets (5 weeks old) were inoculated by subcutaneous route only with the adjuvanted neurotoxin obtained according to the process of example 1.

Two vaccinal dosages were used : 80 mg dosage in the one group, 20 mg dosage in the other group.

One month after the injection, the vaccinated piglets and the control ones were challenged as in examples 3 and 4.

The results are summarized in the following Table IV.

TABLE IV

| Piglets | | Results of the challenge | | | | |
|---|---|---|---|---|---|---|
| | | Mortality without previous symptoms | Eyelid oedema | Ataxia | Convulsions | Paralysis |
| Vaccinated with 80 mg of neurotoxin | 21 | − | − | − | − | − |
| | 22 | − | − | − | − | − |
| | 23 | − | − | − | − | − |
| Vaccinated with 20 mg of neurotoxin | 24 | − | − | − | − | − |
| | 25 | − | − | − | − | − |
| | 26 | − | − | − | − | − |
| Control | 27 | − | − | + | + | − |
| | 28 | − | − | − | − | − |

TABLE IV-continued

| Piglets | Results of the challenge | | | | |
|---|---|---|---|---|---|
| | Mortality without previous symptoms | Eyelid oedema | Ataxia | Convulsions | Paralysis |
| 29 | — | — | — | — | — |

As shown in the examples 3, 4 and 5, none of the vaccinated animals presents symptoms of oedema disease after intravenous challenge with *E. coli* neurotoxin while 9 out of 14 control animals present one or more clinical features of the disease.

EXAMPLE 6

Crude neurotoxin was prepared as described in example 1 up to and including freeze-drying of the crude preparation, suspended in water and adsorbed on Alhydrogel. The preparation was administered by subcutaneous route at a 45 mg dosage unit to 3 week old piglets, one piglet being kept as control.

Three weeks after administration, the piglets were challenged intravenously as in examples 2, 3 and 4 with 2 mg/kg of same crude neurotoxin diluted in phosphate buffered saline (PBS), pH 8.2.

The outcome of the challenge inoculation was fundamentally different from the one following administration of purified neurotoxin and described in examples 2, 3 and 4. In this case two vaccinated piglets showed symptoms characteristic of anaphylactic shock immediately after challenge (violent excitment, trembling, incoordination, cyanosis and died two hours later; the symptoms of the control piglet were vomiting, depression and paralysis at 48 hours after inoculation.

EXAMPLE 7

Crude neurotoxin is prepared as described in example 1 up to and including freeze-drying of the crude preparation.

Alhydrogel (50 ml) in 0.08 M phosphate buffer ($KH_2PO_4$/NaOH, pH 8) is mixed to 100 g of powdered cellulose D-510 (a product sold by MACHEREY-NAGEL, Duren, BDR). A column (2.5 × 30 cm) is packed with the mixture and equilibrated at 4° C. with 0.01 M phosphate buffer ($KH_2PO_4$/NaOH, pH 8).

A 43 mg aliquot of the crude preparation is dissolved in 4.5 ml of 0.01 M phosphate buffer (ph 8) and the solution is poured at the top of the column on which a linear gradient from 0.01 M to 0.4 M phosphate buffer is then applied.

In these conditions, two main peaks appear in the elution profile : the first one is eluted at the 0.01 M phosphate buffer concentration and contains the endotoxin and the second one is eluted at a concentration between 0.25 M and 0.4 M phosphate buffer and contains endotoxin-free neurotoxin which, when examined using the gel filtration technique on Sepharose 6-B described in example 1, presents the same characteristic as the one of the endotoxin free neurotoxin obtained in example 1.

What we claim is:

1. Enterotoxin-free *E. coli* neurotoxin having an average molecular weight of 100,000 and obtained from the supernatant of disrupted cells of a culture of a neurotoxin producing strain of a 0138, 0139 or 0141 *E. coli* serogroup capable of causing oedema disease of piglets.

2. Piglet oedema disease vaccine for intramuscular or subcutaneous administration to piglets which comprises an effective amount of an *E. coli* neurotoxin according to claim 1 adsorbed on an effective amount of an adjuvant selected from the group consisting of aluminium hydroxide and aluminium phosphate.

3. Piglet oedema disease vaccine according to claim 2 wherein the *E. coli* neurotoxin is isolated from the neurotoxin producing *E. coli* strain ATCC 31,165 of the 0139 serogroup.

4. Piglet oedema disease vaccine according to claim 2 wherein the amount of *E. coli* neurotoxin is at least 80 mg.

5. Method of preventing piglet oedema disease comprising administering to piglets a vaccine according to claim 2.

* * * * *